(12) United States Patent
Wolf et al.

(10) Patent No.: US 8,777,613 B2
(45) Date of Patent: Jul. 15, 2014

(54) SYSTEM FOR INSERTION OF IMPLANTS

(75) Inventors: Dietrich Wolf, Oberkochen (DE);
Norbert Bergner, Mannheim (DE)

(73) Assignee: Friadent GmbH, Mannheim (DE)

( * ) Notice: Subject to any disclaimer, the term of this patent is extended or adjusted under 35 U.S.C. 154(b) by 598 days.

(21) Appl. No.: 12/225,603

(22) PCT Filed: Mar. 30, 2007

(86) PCT No.: PCT/EP2007/002888
§ 371 (c)(1),
(2), (4) Date: Mar. 12, 2009

(87) PCT Pub. No.: WO2007/112977
PCT Pub. Date: Oct. 11, 2007

(65) Prior Publication Data
US 2009/0181340 A1    Jul. 16, 2009

(30) Foreign Application Priority Data

Mar. 30, 2006 (DE) .......................... 10 2006 015 215
Nov. 21, 2006 (DE) .......................... 10 2006 055 212

(51) Int. Cl.
*A61C 3/02* (2006.01)
(52) U.S. Cl.
USPC .......................................................... 433/76
(58) Field of Classification Search
USPC ........... 433/8, 51, 70–75, 174; 606/96, 97, 99
See application file for complete search history.

(56) References Cited

U.S. PATENT DOCUMENTS

| | | | | |
|---|---|---|---|---|
| 4,998,881 A | * | 3/1991 | Lauks | 433/173 |
| 5,320,529 A | * | 6/1994 | Pompa | 433/76 |
| 5,641,287 A | * | 6/1997 | Gittleman | 433/75 |
| 5,718,579 A | * | 2/1998 | Kennedy | 433/75 |
| 5,964,591 A | * | 10/1999 | Beaty et al. | 433/173 |
| 5,967,777 A | * | 10/1999 | Klein et al. | 433/75 |
| 5,989,025 A | * | 11/1999 | Conley | 433/76 |
| 6,319,000 B1 | * | 11/2001 | Branemark et al. | 433/75 |

(Continued)

FOREIGN PATENT DOCUMENTS

| | | |
|---|---|---|
| EP | 0328911 | 8/1989 |
| EP | 1502556 | 2/2005 |

(Continued)

*Primary Examiner* — Heidi M Eide
*Assistant Examiner* — Matthew Saunders
(74) *Attorney, Agent, or Firm* — Jordan and Hamburg LLP

(57) ABSTRACT

A system for insertion of implants, in particular dental implants, comprises a splint, which is provided with a bore and which is designed for positioning the implant onto an area intended for the insertion, in particular a bone, and can be placed on the latter. The system also includes an insertion or screwing tool for the implant, and the splint has a guide surface. The system is to be further designed such that the precise insertion of the implant can be predefined with a high degree of reliability. For this purpose, the insertion or screwing tool has a head part to which the implant is connected and which has an outer surface for bringing into engagement with the guide surface, the insertion or screwing tool also comprises a first stop or abutment, and that the splint in the area of the bore comprises or at least indirectly acquires a further stop or abutment, on which the first stop or abutment of the screwing tool comes to rest in order to define the depth of insertion of the implant when it is being screwed in.

12 Claims, 4 Drawing Sheets

(56) References Cited

U.S. PATENT DOCUMENTS

| | | |
|---|---|---|
| 6,514,258 B1 * | 2/2003 | Brown et al. .................. 606/80 |
| 6,537,067 B1 * | 3/2003 | Wennemann ................... 433/76 |
| 2002/0137003 A1 * | 9/2002 | Knapp ........................... 433/76 |
| 2005/0170311 A1 * | 8/2005 | Tardieu et al. ................. 433/76 |
| 2006/0093988 A1 * | 5/2006 | Swaelens et al. .............. 433/76 |
| 2006/0188840 A1 * | 8/2006 | Verban, Jr. .................... 433/75 |

FOREIGN PATENT DOCUMENTS

| | | | |
|---|---|---|---|
| EP | 1502556 A2 * | 2/2005 | |
| EP | 1759658 | 3/2007 | |
| EP | 1759658 A1 * | 3/2007 | ............... A61C 1/08 |
| WO | WO-97/49351 | 12/1997 | |
| WO | WO-99/26540 | 6/1999 | |
| WO | WO 2004098435 A2 * | 11/2004 | |

* cited by examiner

SYSTEM FOR INSERTION OF IMPLANTS

BACKGROUND OF THE INVENTION

The invention relates to an arrangement for inserting implants, in particular dental implants.

Known from US 2005/0170311 A1 is such an arrangement, which contains a splint, embodied as a template, for positioning the implant or implants. The splint is produced based on data that are generated by means of computer tomography (CT), X-ray, or some other device that images the bone, in particular the jaw bone, in order to be able to plan and specify in a defined manner the position required for the implant, taking into account anatomical, surgical, and also aesthetic factors. The splint is adapted to the individual situation and factors and contains at least one continuous bore for receiving a guide sleeve having a through-bore, using which it is possible to specify the exact orientation and positioning of the bore for the implant. Furthermore provided is a bore sleeve that has a through-bore, that can be used in the guide sleeve of the splint, and the interior diameter of which is matched to the exterior diameter of the drill bit for adding the bore to the bone. The drill bit contains an annular collar or stop that can be positioned on the free upper edge of the bore sleeve in order to specify the depth of the bore in the bone. Furthermore, the splint is used for adding the implants, to which special fastening bodies are joined by means of screws. The fastening bodies each contain one cylindrical area that faces the implant and the exterior diameter of which is matched to the interior diameter of the guide sleeve fixed in the splint. The fastening body contains an area that faces away from the implant and that has for instance contact surfaces embodied as a hexagon for an insertion tool. In the axial direction between the two aforesaid areas the fastening body has a flange that is positioned against the free upper edge of the guide cylinder to limit the placement depth of the implant.

The flange has a significantly larger diameter than the cylindrical area so that problems can occur when tight space is a problem. The fastening body has an axial length that is not insignificant, so that handling while the implant is being inserted is rendered significantly more difficult in terms of the tight space issues in the oral cavity. Since as is known implant systems have implants that have different diameters, a substantial number of such fastening bodies are needed. The placement and exact positioning of so-called miniature implants or mini-implants having exterior diameters on the order of magnitude of 1 mm and less is not possible with nothing further, that are primarily embodied in a single piece and enable minimally invasive transgingival insertion. In practice, problems result when placing the implants in the implant bed, which has been prepared by means of the aforesaid arrangement, especially with mini-implants, so that it is difficult for the surgeon to control the placement depth of the implant and furthermore, with respect to the quite large distance from the insertion tool to the implant due to the fastening body, undesired tilting moment or rotations can be caused that lead to incorrect positioning.

SUMMARY OF THE INVENTION

Proceeding from this point, the object of the invention is to avoid the cited disadvantages and refine the arrangement such that it is possible to specify with great reliability the exact placement of the implant, in particular in addition for the exact positioning of the bore. The arrangement should have a simple and functionally reliable structure and should ensure that handling is reliable and problem-free when adding the bore to the bone and/or when inserting the implant.

The inventive arrangement is distinguished by a functionally appropriate design and makes it possible to place the implant at a specifiably defined placement depth with no problem. The insertion or screwing (hereinafter "insertion") tool is joined directly to the implant and possesses a head part, the exterior surface of which is used for guidance during insertion. The exterior diameter of the head part is matched to the interior diameter of the interior surface of the recess and/or bore provided in the splint. Insertion tools that have the same exterior dimensions or the exterior dimensions of which match are advantageously used for implants having different exterior diameters. Since no special fastening bodies are provided between the insertion tool and the implant, there is no associated production and/or provision complexity. The splint is advantageously embodied for receiving a sleeve for placing the implant, the interior diameter of which is at least partially matched to the exterior diameter of the implant. This sleeve, hereinafter referred to as the placement sleeve, has a stop or positioning surface or abutment (hereinafter "first stop surface" or "stop"), and, corresponding thereto, in particular the insertion tool possesses a second stop or positioning surface or abutment (hereinafter "second stop surface" or "stop") such that when inserting the implant and upon positioning of the aforesaid stop surfaces further insertion is prevented and thus the exact placement depth for the implant is prespecified in a defined manner. The stop surfaces are preferably provided within the recess and/or bore of the at least one sleeve. Furthermore, in accordance with the invention the placement sleeve, can be omitted, especially in miniature implants, and the stop surface can be an integral component of the splint or can be embodied in a single piece therewith. The stop surfaces can be embodied as steps, annular collars, or the like, of the placement sleeve, guide sleeve, or bore sleeve or splint, on the one hand, and of the drill bit or of the insertion tool, on the other hand. It is particularly significant, especially in implants having small exterior diameters and in particular in miniature implants, that the exterior diameter of the head part of the placement tool is significantly larger than that of the miniature implant, so that exact placement and/or positioning is assured in a particularly advantageous manner.

BRIEF DESCRIPTION OF THE DRAWINGS

The invention is explained in greater detail in the following, but is not restricted thereby.

FIG. 1 provides a schematic depiction of a jaw 2, including mucosa, and the splint 4 provided thereupon for positioning the bore to be added and the implant. In a recess or bore 6 the splint 4 contains a guide sleeve 8 that is usefully securely joined to the splint 4, for instance by gluing. Alternatively the guide sleeve 8 can be arranged detachable or placeable in the splint 4. Arranged in the guide sleeve 8 is a detachable bore sleeve 10, the guide sleeve 8 having first, usefully radially interiorly disposed positioning elements 12 and furthermore the bore sleeve 10 having radially exteriorly disposed second positioning elements 14. The positioning elements 12 and 14 are embodied in particular as steps that correspond to one another and facilitate axial positioning of the bore sleeve 10 in terms of a longitudinal axis 16. The bore sleeve 10 furthermore contains a stop surface 18, preferably interiorly disposed, for the purpose of specifying the bore depth of the drill bit (not shown here). Alternatively, in accordance with the drawing the upper end surface 20 can act as the stop for a correspondingly embodied drill bit.

Moreover, in the framework of the invention the guide sleeve 8 can be embodied as an integral component of the splint 4 and/or can be embodied in a single piece therewith. Furthermore, in the framework of the invention the bore sleeve 10 can also be embodied as an integral component of the splint 4 and/or in a single piece therewith, the splint 4 comprising a material that is strong enough and/or hard enough to prevent damage from the drill bit.

Figure 1:
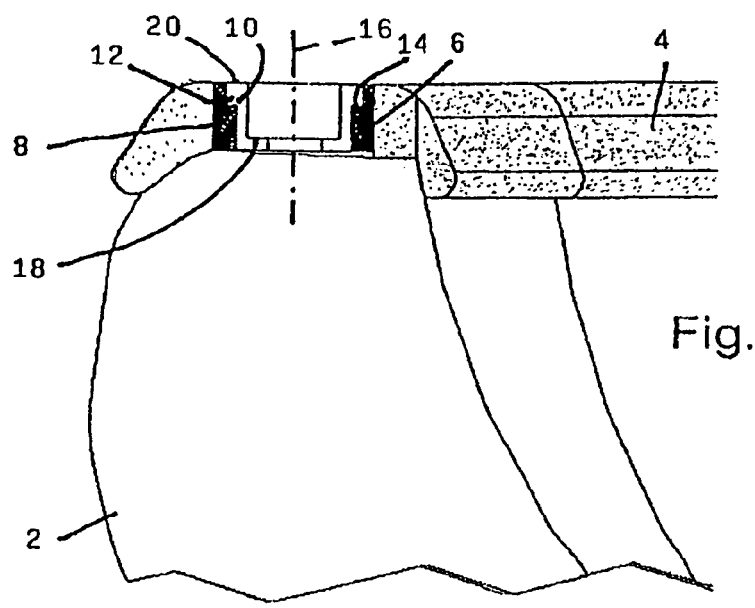
FIG. 1 is a depiction of the jaw with the splint of the inventive arrangement.
Figure 2:
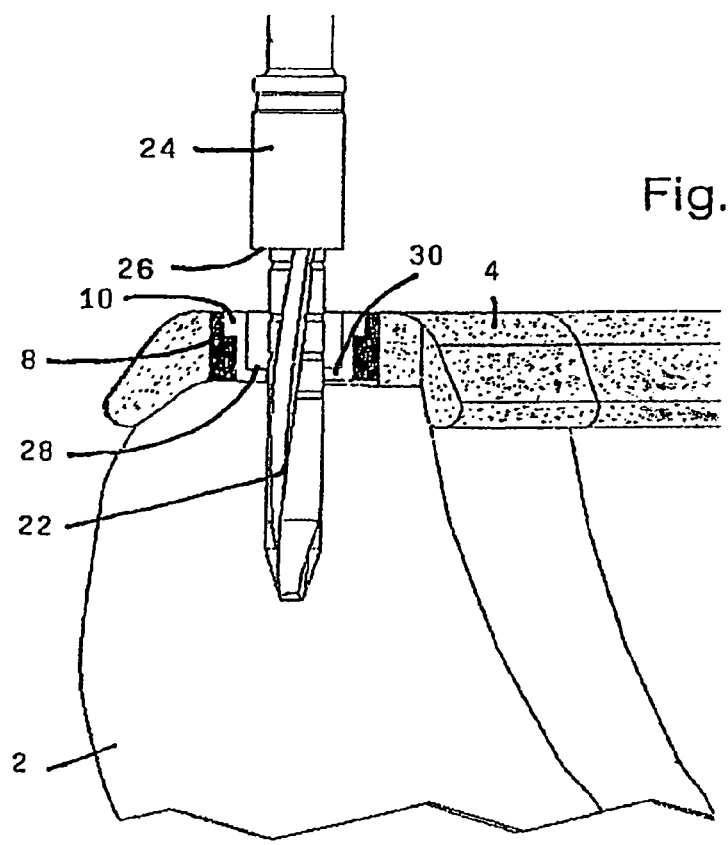
FIG. 2 is a depiction in accordance with FIG. 1 with a drill bit in a first axial position.
Figure 3:
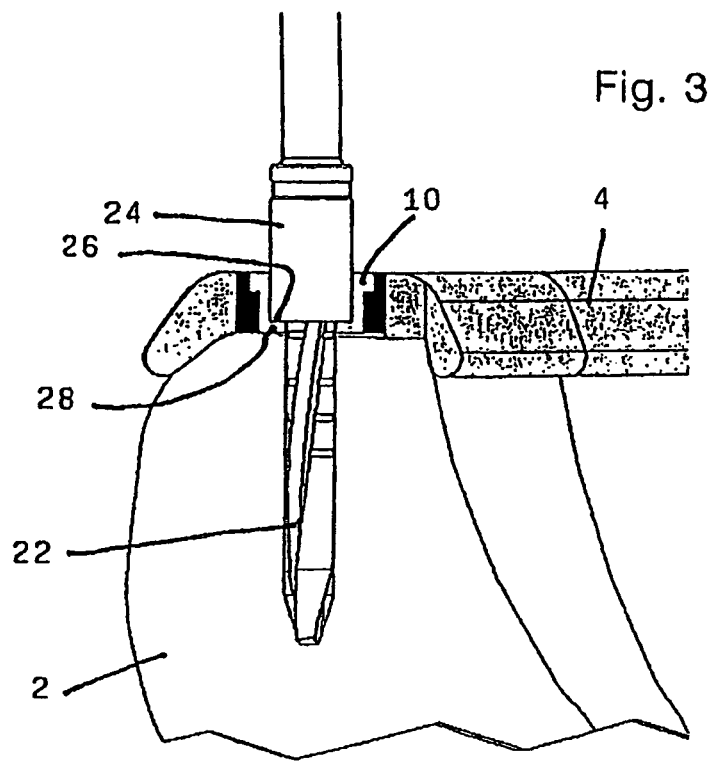
FIG. 3 is a depiction in accordance with FIG. 1 with the drill bit shown in FIG. 2 in a second axial position.

FIGS. 2 and 3 additionally depict the drill bit 22 that is used in a drill 24. The drill 24 contains a positioning surface 26 that is embodied corresponding to the positioning surface 28 in the bore sleeve 10. Also, the exterior diameter of the drill 24 and the interior surface of the bore sleeve 10 are matched to one another, just like the exterior diameter of the drill bit 22 and the interior diameter of the web 30 that in accordance with the drawing is arranged in the direction of the jaw 2 below the positioning surface 18 in the bore sleeve 10. In accordance with FIG. 3, the lower positioning surface 26 of the drill 24 is positioned against the positioning surface 28 of the bore sleeve 10 which defines a drill positioning stop surface of the web 30, and the specified bore depth for the drill bit 22 is attained.

Figure 4:
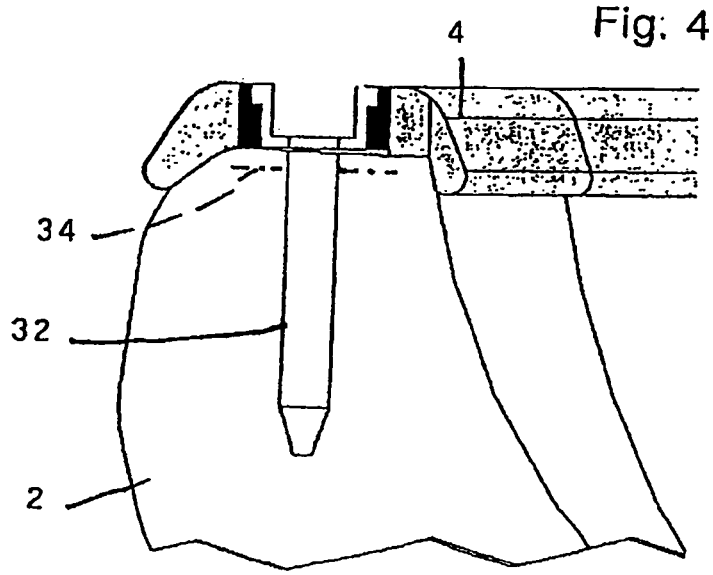
FIG. 4 is a depiction in accordance with FIG. 1 after the bore has been added to the jaw.

In accordance with FIG. 4, the jaw 2 contains the placement bore 32 or the prepared implant bed for the implant. It should be noted that the splint 4 is placed on the jaw 2, the fringe or transition region between the mucosa and the jaw bone being indicated with the broken line 34. It is furthermore expressly noted that the inventive arrangement is used in particular for transgingival implants and is embodied to be minimally invasive for a so-called flapless insertion with great precision.

Furthermore, in the framework of the invention, instead of a single bore sleeve, a plurality of bore sleeves for an implant system can be provided, the exterior geometries of which are consistent and are matched to the interior geometry of the guide sleeve or the recess in the splint. Especially in the area of the aforesaid web these bore sleeves have interior diameters that are matched to the different exterior diameters of the drill bits that are used. Thus for instance initially a pre-bore or pilot bore can be added to the jaw using a comparatively narrow drill bit, in order to then prepare the implant bed with the required dimensions using one or a plurality of drill bits that have correspondingly larger exterior diameters.

Figure 5:
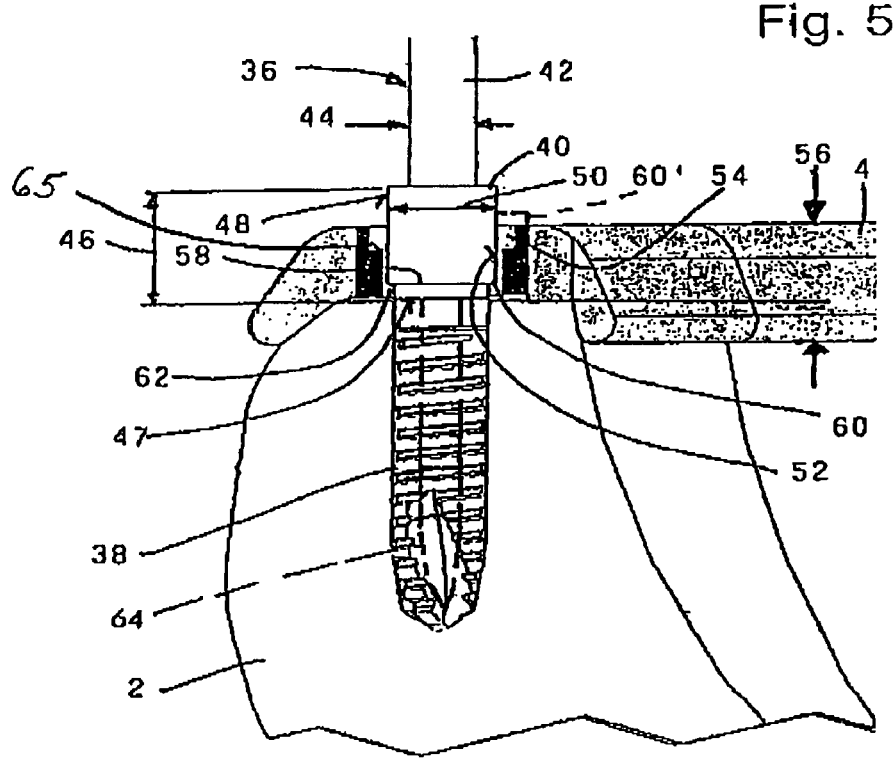
FIG. 5 is a depiction with the insertion tool and implant.

FIG. 5 depicts an insertion tool 36 by means of which the implant 38 is inserted into the jaw 2. In a preferred manner the insertion or placement tool 36 and the implant 38 are provided preassembled so that in particular after the bore has been added to the jaw the implant 38 can be inserted without additional aids. The insertion or placement tool 36 contains a head part 40 that connects to the implant 38 and directly to a shaft 42, the exterior diameter 44 of which is preferably significantly smaller than the exterior diameter 50 of the head part 40. The implant 38 has an axial end face 45 associated with the head part 40. Axially the head part 40 has a length 46 and an exterior surface 48 having the diameter 50. Moreover, provided within the splint 4 is an axially continuous recess or guide surface 52 against the interior surface of which the head part 40 is positioned and/or guided during insertion, the interior surface of the recess 52 forming the guide surface. The exterior diameter 50 of the head part 40 is at least approximately the same size as the interior diameter of the recess 52. The length 46 of the head part 40 is at least the same size as the thickness 56 of the splint 4 in the insertion area. Preferably, the length 46 of the head part 40 is greater than the diameter 50 thereof by a specified factor, the factor being a maximum of 2, preferably a maximum of 1.6, and in particular 1.4. Moreover, the entire axial length of the placement tool 36 is specified relatively short, the length advantageously being specified greater than the length 46 by a maximum of a factor of 3, in particular by a maximum of a factor of 2.5. In accordance with the invention the cylindrical head part 40 is positioned with its axial end face 47 directly against the associated end face 45 of the implant 38. Due to the quite limited length of the placement tool 36 thus specified, lifting or tilting movements by the placement tool 36 are kept small and largely avoided while the implant 38 is placed into the jaw 2, which renders easier exact positioning of the implant 38. Moreover handling during placement of the implant is improved due to the small dimensions of the placement tool.

As depicted, the recess and/or guide surface 52 is disposed in the placement sleeve 54. In one special embodiment of the invention, it is possible to omit the addition of the bore and furthermore of the sleeves explained in this regard and the implant, in particular a miniature implant, can be inserted by means of a preferably self-cutting thread. Furthermore the insertion tool 36 and the implant 38 can be joined in a suitable manner and/or by means of suitable means (not shown in greater detail) by the surgeon.

The placement or insertion tool 36 includes a stop 58, inventively embodied in the area of the axial end face 47 of the head part 40 and/or as a short step or annular collar, for exactly pre-specifying a defined insertion depth for the implant. The splint 4 and in particular the placement sleeve 54 includes another stop 60, to which the stop 58 of insertion tool 36 corresponds. The stops 58, 60, which in accordance with FIG. 5 are preferably disposed in the lower end area of the splint 4, which end area faces the jaw 2, and/or therein, limit the depth the implant 38 penetrates into the jaw 2 when it is being inserted. The exterior geometry of the placement sleeve 54 is adapted to the interior geometry of the first guide sleeve 8 so as to provide positioning elements 65 of the placement sleeve that rest on the positioning elements 12 of the guide sleeve 8. The interior diameter of the placement sleeve 54 or of the recess 52 provided therein is substantially the same size as the exterior diameter of the head part 40 of the insertion tool 36, specifically apart from the additional radially inwardly oriented web 62 of the placement sleeve 54. Preferably, the additional stop 60 is disposed inside the splint 4 so that when the end position is reached the additional stop 60 of the insertion tool 36 is disposed inside the splint. In the framework of the invention, alternative to the stop 60 the insertion tool 36 can have a stop 60', arranged outside of or above the splint 4, that is indicated with the broken line and that usefully comes to be positioned against the upper end surface of the placement sleeve 54, according to FIG. 5 upon reaching maximum insertion depth.

Moreover, indicated by means of the broken line in FIG. 5 is a miniature implant 64 that has a significantly smaller diameter than the implant 38. It is assumed that the depicted implant 38 is the implant that has the largest exterior diameter in a system of implants having different exterior diameters. In the framework of the invention, for all of the implants in an implant system, including miniature implants, that have an exterior diameter equal to or smaller than 1 mm, the same insertion tool 36 is provided and/or in particular an insertion tool 36 is provided that is consistent with the embodiment of the head part 40, so that in particular the complexity of producing and providing the insertion tool or tools is significantly reduced. Moreover, it has proved particularly advantageous to have each placement sleeve 54 be of diameter consistent with the bore sleeve, in particular for the implant having the largest diameter in the implant system, so that the same bore sleeve may be used with the placement sleeve. Using the inventive implant system significantly simplifies and reduces the components for the implant set, including accessory aids, specifically the aforesaid sleeves.

In one special embodiment of the invention the first sleeve and/or the bore sleeves can be omitted, the implant as a transgingival implant being placed directly and without bores or preparation of an implant bed in the jaw or jaw bone. This embodiment is provided in particular for mini-implants, the exterior diameter of which are specified on the order of magnitude of 1 mm and where necessary even smaller. Even with such transgingival and/or single-piece implants that have a small diameter, the arrangement has the insertion tool having a stop surface and furthermore the insertion tool has a stop surface corresponding thereto for specifying an exactly defined placement depth for the implant.

Figure 6:
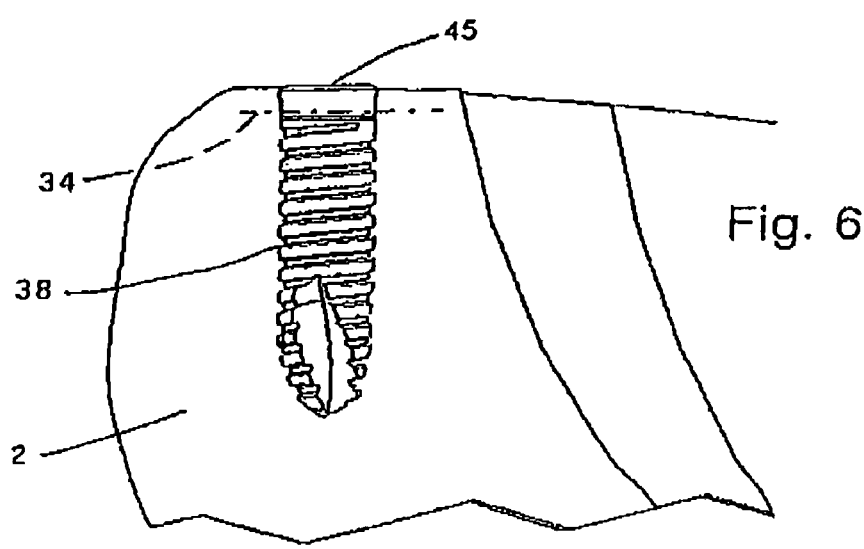
FIG. 6 schematically depicts the jaw with implant after insertion.

FIG. 6 depicts the implant 38 completely implanted in the jaw 2 after the splint has been removed. The single-piece implant 38 is inserted transgingivally, the fringe or transition region between mucosa and jaw bone again being indicated by means of the broken line 34.

Figure 7:
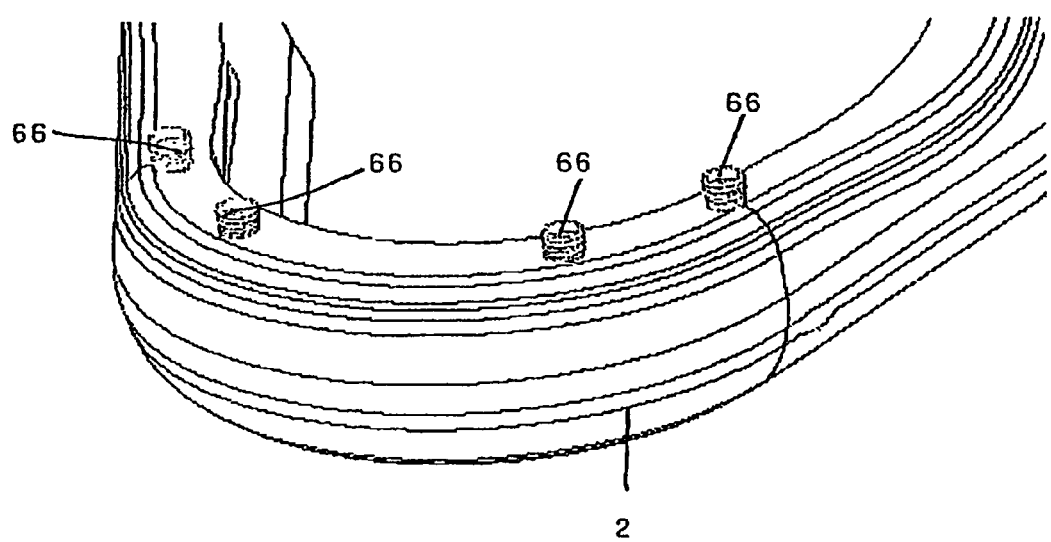
FIG. 7 schematically depicts the jaw with the anchoring bodies of four implants.

FIG. 7 is a schematic depiction of the jaw 2 after four implants have been inserted. The implants are completely inserted into the jaw in accordance with FIG. 6, and what is visible is only the anchoring bodies 66 for crowns, bridges, and the like that are connected to the implants.

The invention claimed is:

1. An implant arrangement for inserting in a jaw a dental implant having a given diameter, comprising
    a splint having a bore therethrough and being shaped to be received over at least a portion of the jaw with the bore substantially axially aligned with a site on the jaw into which said implant is to be inserted,
    a guide sleeve arranged within the bore,
    an annular guide surface formed within a placement sleeve received in the guide sleeve, the guide surface being of greater diameter than a maximum diameter of said implant,
    an insertion tool for screwing in the implant into the jaw and having a head for connection to said implant so as to connect the insertion tool and implant together, the head having an annular exterior surface of smaller diameter than said guide surface for sliding engagement with the guide surface, the insertion tool having a first stop surface being formed by a surface of the head of the insertion tool, a second stop surface being formed within the placement sleeve received in the bore in a plane substantially orthogonal to an axis of the bore, the first and second stop surfaces being located so as to abut against each other when said implant has been inserted by the insertion tool to a predetermined depth in the jaw so that said abutment defines an insertion depth of the implant, and in which
    a bore sleeve is received in the bore for guiding a drill and a drill bit to a predetermined bore depth as the drill bit drills the jaw in preparation for insertion of said implant, the bore sleeve being received in the guide sleeve and the bore sleeve and the guide sleeve comprising respectively corresponding radially disposed exterior and interior stepped positioning elements formed thereon that engage with each other to alignably position the bore sleeve in the guide sleeve and in the bore in an axial direction of the bore along a longitudinal axis of the bore, the bore sleeve comprising a drill positioning stop surface distal an outermost top peripheral surface of the splint and against which a surface of the drill abuts prior to the bore sleeve being removed from the guide sleeve upon completion of drilling of the jaw, and in which
    upon removal of the bore sleeve, a stepped positioning element of the placement sleeve corresponding to said stepped positioning element of the guide sleeve engage with each other so as to axially align and seat said second stop surface of the placement sleeve during insertion of the implant, and
    each of the above stepped positioning elements comprising, when viewed in cross-section, a laterally and vertically extending portion relative to the longitudinal axis of the bore that engage each other upon engagement of the bore sleeve and the placement sleeve with the guide sleeve, said engagement of the respective sleeves at the respective laterally and vertically extending portions comprising one or more points of engagement located substantially beneath an outermost top peripheral surface of each of the respective sleeves and the outermost top peripheral surface of the splint.

2. The implant arrangement according to claim 1, wherein the axial length of the head is at least equal to a thickness of the splint.

3. The implant arrangement according to claim 2, wherein a ratio of the axial length of the head to the thickness of the splint is a maximum of 2.

4. The implant arrangement according to claim 2, wherein a ratio of the axial length of the head to the thickness of the splint is a maximum of 1.5.

5. The implant arrangement according to claim 1, wherein the head has an axial end face for abutting against an axial end surface of said implant.

6. The implant arrangement according to claim 1, wherein said insertion tool further comprises a shaft connected to and substantially coaxial with the head, an exterior diameter of the shaft being substantially smaller than the exterior diameter of the head.

7. The implant arrangement according to claim 1, wherein the guide sleeve is detachable from the splint.

8. The implant arrangement according to claim 1, wherein the guide sleeve is securely affixed to the splint.

9. The implant arrangement according to claim 1, wherein the second stop surface comprises an upper annular surface of an annular web proximate a distal axial end of the bore.

10. The implant arrangement according to claim 1, wherein the placement sleeve has a diameter slightly greater than a diameter of a drill bit for guiding the drill bit as the drill bit drills the jaw in preparation for insertion of said implant.

11. The implant arrangement according to claim 1, wherein an interior surface of the bore sleeve is matched to the exterior diameter of the drill.

12. An implant arrangement for inserting in a jaw a dental implant having a given diameter, comprising
    a splint having a bore therethrough and being shaped to be received over at least a portion of the jaw with the bore substantially axially aligned with a site on the jaw into which said implant is to be inserted, a guide sleeve arranged within the bore, an annular guide surface formed within a placement sleeve received in the guide sleeve, the guide surface being of greater diameter than a maximum diameter of said implant, an insertion tool for screwing in the implant into the jaw and having a head for connection to said implant so as to connect the insertion tool and implant together, the head having an annular exterior surface of smaller diameter than said guide surface for sliding engagement with the guide surface, the insertion tool having a first stop surface being formed by a surface of the head of the insertion tool, a second stop surface being formed within the placement sleeve received in the bore in a plane substantially orthogonal to an axis of the bore, the first and second stop surfaces being located so as to abut against each other when said implant has been inserted by the insertion tool to a predetermined depth in the jaw so that said abutment defines an insertion depth of the implant, and in which a bore sleeve is received in the bore for guiding a drill and a drill bit to a predetermined bore depth as the drill bit drills the jaw in preparation for insertion of said implant, the bore sleeve being received in the guide sleeve and the bore sleeve and the guide sleeve comprising respectively corresponding radially disposed exterior and interior stepped positioning elements formed thereon that engage with each other to alignably position the bore sleeve in the guide sleeve and in the bore in an axial direction of the bore along a longitudinal axis of the bore, the bore sleeve comprising a drill positioning stop surface distal an outermost top peripheral surface of the splint and against which a surface of the drill abuts prior to the bore sleeve being removed from the guide sleeve upon completion of drilling of the jaw, and in which upon removal of the bore sleeve, a stepped positioning element of the placement sleeve corresponding to said stepped positioning element of the guide sleeve engage with each other so as to axially align and seat said second stop surface of the placement sleeve during insertion of the implant, and each of the above stepped positioning elements comprising, when viewed in cross-section, a laterally and vertically extending portion relative to the longitudinal axis of the bore that engage each other upon engagement of the bore sleeve and the placement sleeve with the guide sleeve, said engagement of the respective sleeves at the respective laterally and vertically extending portions comprising one or more points of engagement located substantially beneath an outermost peripheral surface of each of the respective sleeves and the outermost top peripheral surface of the splint, and whereby a surface of the bore sleeve defines a web comprising an abutment surface extending radially inward toward the longitudinal axis of the bore so as to define the drill positioning stop surface which limits an insertion depth of the drill bit, and a surface of the placement sleeve defines a web comprising an abutment surface extending radially inward toward the longitudinal axis of the bore so as to define the second stop surface serving to limit an insertion depth of the implant and insofar as such depth is defined in accordance with the abutment of said first and second stop surfaces.

\* \* \* \* \*